United States Patent

Rufer et al.

[11] 3,966,732
[45] June 29, 1976

[54] NITROIMIDAZOLYL PYRIMIDINES

[75] Inventors: Clemens Rufer; Eberhard Schroder; Hans-Joachim Kessler, all of Berlin, Germany

[73] Assignee: Schering Aktiengesellschaft, Berlin & Bergkamen, Germany

[22] Filed: Apr. 14, 1975

[21] Appl. No.: 568,117

Related U.S. Application Data

[62] Division of Ser. No. 331,114, Feb. 9, 1973, Pat. No. 3,920,655.

[30] Foreign Application Priority Data

Feb. 19, 1972 Germany............................ 2208518
Nov. 7, 1972 Germany............................ 2255079

[52] U.S. Cl................. 260/256.4 C; 260/256.5 R; 260/309.6; 260/256.4 R
[51] Int. Cl.² ........................................ C07O 239/00
[58] Field of Search............. 260/256.5 R, 256.4 N, 260/256.4 R, 256.4 C

[56] References Cited
UNITED STATES PATENTS
3,880,852    4/1975    Cole et al.................... 260/256.5 R OTHER PUBLICATIONS
Merck Inpex 8th Ed. p. 695 (1968).

*Primary Examiner*—Leonard Schenkman
*Attorney, Agent, or Firm*—Millen, Raptes & White

[57] ABSTRACT

Nitroimidazolyl pyrimidines of the formula

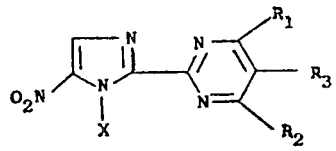

and physiologically acceptable acid addition salts thereon wherein X is alkyl of 1–4 carbon atoms, $R_1$ and $R_2$ each are a hydrogen atom, alkyl of 1–4 carbon atoms, phenyl triflouromethyl or a monocyclic heterocyclic ring and $R_3$ is a hydrogen atoms, alkyl of 1–4 carbon atoms, hydroxyalkoxy of 2–4 carbon atoms or an ester thereof of an alkanocarboxylic acid of 1–4 carbon atoms, oxoalkyl of 8–6 carbon atoms, or, when $R_1$ or $R_2$ is phenyl, alkylene having 1–2 carbon atoms in the chain joined to the 2-position of the phenyl ring possess trichomonicidal activity.

10 Claims, No Drawings

NITROIMIDAZOLYL PYRIMIDINES

This is a division of application Ser. No. 331,114, filed Feb. 9, 1973, now U.S. Pat. No. 3,920,655.

BACKGROUND OF THE INVENTION

The effectiveness of nitroimidazoles against trichomonads has been known since the discovery of the antibiotic azomycin (2-nitroimidazole, S. Nakamura and H. Umezawa, J. Antibiotics (Tokyo), 9 A, 66 [1955]). However, this compound and other 2-nitroimidazoles proved to be no more effective in vitro than metronidazole (5-nitro-2-methyl-1-(2-hydroxyethyl)-imidazole), G. C. Lancini, E. Lazzari, R. Pallanea, 11 Farmaco Ed Sc. 21, 278 [1966]) and the $ED_{50}$- and $LD_{50}$-values were considerably less favorable (E. Grunberg. F. Titsworth, Antimicrobial Agents and Chemotherapy, 1965, 1966, 478). Only from the 5-nitroimidazoles evolved the best among a large number of synthesized compounds, viz., the commercial preparation metronidazole (C. Cosar, "Arzneimittelforschung", 16, 23 [1966]). See also French Pat. No. 1,212,028 which has a minimum inhibitory concentration of 2.5 g/ml. against Trichomonas vaginalis.

It has now been discovered that the known 1-substituted 5-nitro-2-imidazolyl-iminocarboxylic acid esters can be removed with ammonia or ammonium salts to produce novel 1-substituted 5-nitro-2-imidazolyl-carboxamidines, which also have trichomonicidal activity, which compounds can then be reacted with β-dicarboxy compounds and or the derivatives thereof to produce 2-(5-nitro-2-imidazolyl)-pyrimidines, which are more effective than metronidazole in trichomonacidal activity.

SUMMARY OF THE INVENTION

The compounds of this invention are nitroimidazolyl pyrimidines of the general Formula I

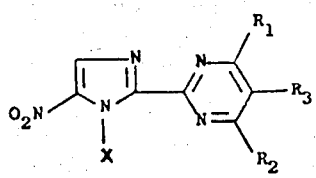

and physiologically acceptable salts thereof, wherein X is alkyl of 1–4 carbon atoms, $R_1$ and $R_2$, which can be alike or different, are a hydrogen atom, alkyl of one to four carbon atoms, phenyl, trifluoromethyl or a thienyl group, and $R_3$ is a hydrogen atom, alkyl of 1–4 carbon atoms, hydroxyalkoxy of 2–4 carbon atoms, which can be esterified by alkanoic acid of 1–4 carbon atoms, i.e., alkanoyloxyalkoxy, oxoalkyl, i.e., keto substituted alkyl, containing a total of 3–6 carbon atoms, or when $R_1$ or $R_2$ is phenyl, an alkylene having 1 – 2 carbon atoms in the chain joined to the 2-position of the phenyl ring.

DETAILED DISCUSSION

Examples of alkyl of 1–4 carbon atoms are methyl, ethyl, n-propyl, isobutyl, etc., preferably methyl.

Examples of hydroxyalkoxy and esters thereof of an alkanoic acid are hydroxyethoxy, 2-hydroxypropoxy, 3-hydroxypropoxy, aceloxyethoxy, propionyloxyethoxy and 3-acetoxypropoxy.

Examples of oxoalkyl are acetylmethyl, acetylethyl and propionylmethyl.

Examples of pyrimidine groups of Formula I wherein $R_1$ or $R_2$ is phenyl and $R_3$ is alkylene are 5,6-dihydrobenzo[h]quinazoline and 5H-indeno[1.2-d]-pyrimidine.

Examples of specific classes of compounds of Formula I are those wherein $R_1$ is H, $CH_3$ or $CF_3$; $R_3$ is H, hydroxyethoxy, acetoxyethoxy, acetylethyl, ethyl; and $R_2$ is $R_1$, phenyl, thienyl or $R_3$ is phenyl and $R_2$ is alkylene joined thereto, especially those wherein X is methyl.

Examples of physiologically acceptable acids which can be employed to form the acid addition salts of this invention are inorganic acids, e.g., hydrochloric acid, sulfuric acid, etc., and organic mono-, di- and tricarboxylic acids, e.g., acetic acid, propionic acid, lactic acid, citric acid, benzoic acid, succinic acid, heptagluconic acid, etc. The exact nature of the acid is not critical, so long as it forms a physiologically acceptable acid addition salt.

The novel compounds of this invention can be produced in a conventional manner, for example, by reacting an amidine of the general Formula II

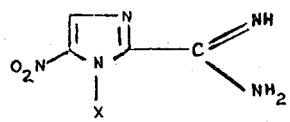

wherein X has the values given above, or a salt thereof, preferably the hydrochloride.

With a β-dicarbonyl compound of the general Formula III

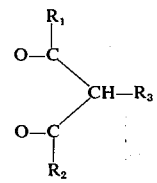

wherein $R_1$, $R_2$ and $R_3$ have the values given above, or a reactive functional derivative thereof, and subsequently saponifying any acyloxy groups present in the condensation product to hydroxy groups, or esterifying free hydroxy groups, and optionally converting the compounds into the salts thereof withh inorganic or organic acids.

Suitable derivatives of the dicarbonyl compound are reactive derivatives such as, for example, the acetal or, if $R_1$ and $R_2$ both are H, an enamine.

The reaction of the amidine (II) and/or the salt thereof, the latter optionally mixed with ammonium chloride, with the β-dicarbonyl compounds or the derivatives thereof can be effected in the absence or in the presence of a solvent, e.g., acetic acid, acetic anhydride, dimethylformamide, alcohol, to which can be added an acidic and/or alkaline catalyst.

The novel compounds exhibit good antimicrobial activity, especially against protozoa and, among these, specifically against Trichomonas vaginalis, as demonstrated by the several exemplary compounds whose activity is compared with metronidazole hereinbelow:

| Compound | Minimum Inhibitory Concentration Against Trichomonas Vaginalis (μg. ml.) |
|---|---|
| 4,6-Dimethyl-2-(5-nitro-1-methyl-2-imidazolyl)-primidine | 0.4 |
| 2-(5-Nitro-1-methyl-2-imidazolyl)-4-methyl-5,6-dihydrobenzo[h]quinazoline | 0.1 |
| 4-Trifluoromethyl-2-(5-nitro-1-methyl-2-imidazolyl)-6-(2-thienyl)-pyrimidine | 0.2 |
| 4-Methyl-6-phenyl-2-(5-nitro-1-methyl-2-imidazolyl)-pyrimidine | 0.2 |
| Metronidazole (in own test) | 1.6 |

The novel compounds can be administered topically or systemically in the pharmaceutically customary forms of application, such as pills, dragees, capsules, vaginal tablets, elixirs, etc., in the same manner as metronidazole.

Tablets, for example, can contain 0.1–0.5 g. of effective substance and 0.1–5 g. of a pharmacologically indifferent excipient. Suitable excipients for tablets are, for instance: lactose, amylose, talc, gelatin, magnesium stearate, etc.

Suitable for topical application are powders, solutions, suspensions, aerosols, and vaginal tablets, and for parenteral application, aqueous and oily solutions or suspensions.

The amidines and or the salts thereof utilized as the starting material can be produced in a conventional manner, for example by reacting known imino esters of the general Formula IV

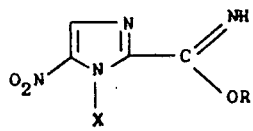

wherein X has the values given above and R is alkyl of 1–4 carbon atoms, with ammonia or an ammonium salt analogously to the preparation below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

PREPARATION 9.9 g. (50 millimoles) of the ethyl ester of 5-nitro-1-methyl-2-imidazolyl-iminocarboxylic acid and 2.7 g. (50 millimoles) of pulverized ammonium chloride are boiled for 72 hours in methanol. After evaporation of the solvent, the residue is digested in the hot state with 100 ml. of etyl acetate: yield: 6.1 g. (47% of theory) of an equimolar mixture of 5-nitro-1-methyl-2-imidazolyl-carboxamidinium chloride and ammonium chloride; m.p. 225°–227° C.

0.52 g. (2 millimoles) of this mixture and 0.55 g. (4 millimoles) of potassium carbonate are agitated in 10 ml. of acetone for 48 hours to give the free amidine, 5-nitro-1-methyl-2-imidazolyl-carboxamidine. After filtration, the filtrate is concentrated and the remaining free amidine is recrystallized from ethyl acetate. Yield: 0.14 g.–40 % of theory, m.p. 144°–146° C.

EXAMPLE 1

4,6-Dimethyl-2-(5-nitro-1-methyl-2-imidazolyl)-pyrimidine 0.52 g. (2 millimoles) of an equimolar mixture of 5-nitro-1-methyl-2-imidazolyl-carboxamidinium chloride and ammonium chloride, 0.21 g. (2.1 millimoles) of acetylacetone, and 0.33 g. of anhydrous sodium acetate are boiled in 4 ml. of acetic acid for 2 hours. Thereafter, the reaction mixture is concentrated to dryness, the residue is triturated with water, and recrystallized from isopropanol. Yield: 0.32 g. (69% of theory), m.p. 148°–150° C.

EXAMPLE 2

2-(5-Nitro-1-methyl-2-imidazolyl)-pyrimidine

The compound is obtained analogously to Example 1 with malonic dialdehyde tetraethylacetal; m.p. 194°–196° C.

EXAMPLE 3

5-(2-Acetoxyethoxy)-2-(5-nitro-1-methyl-2-imidazolyl)pyrimidine

The compound is obtained analogously to Example 1 with 3-dimethylamino-2-(2-hydroxyethoxy)-acrolein; in this process, acetic anhydride can also be employed in place of acetic acid. After concentration of the reaction solution, the residue is mixed with water, the product is extracted with ethyl acetate, and the residue of the ethyl acetate extract is triturated with methanol; m.p. 148°–150° C.

EXAMPLE 4

5-(2-Hydroxyethoxy)-2-(5-nitro-1-methyl2-imidazolyl)pyrimidine Hydrochloride 0.2 g. of 5-(2-acetoxyethoxy)-2-(5-nitro-1-methyl-2-imidazolyl)-pyrimidine is refluxed in 5 ml. of ethanol with 2.5 ml. of concentrated hydrochloric acid. After concentration under vacuum, the residue is recrystallized from ethyl acetate; m.p. 158°–160° C.

EXAMPLE 5

5-(2-Hydroxyethoxy)-2-(5-nitro-1-methyl-2-imidazolyl)pyrimidine Hydrochloride 0.78 g. (5 millimoles) of 3-dimethylamino-2-(2-hydroxyethoxy)-acrolein and 1.3 g. (5 millimoles) of an equimolar mixture of 5-nitro-1-methyl-2-imidazolyl-carboxamidinium chloride and ammonium chloride are added to 5 ml. of 1N sodium methylate solution in methanol. After refluxing for 20 hours, the methanol is distilled off, the residue in maintained at 80° C. for 30 minutes, and mixed with water. The product is extracted with ethyl acetate, the ethyl acetate is concentrated, and the residue is digested with isopropanol. The thus-obtained free base is converted, with methanolic hydrochloric acid, into the hydrochloride, m.p. 158°–160° C.

The same product is obtained by heating equimolar amounts of 5-nitro-1-methyl-2-imidazolyl-carboxamidine and 3-dimethylamino-2-(2-hydroxyethoxy)-acrolein in dimethylformamide or without solvent and converting the mixture thus obtained — optionally after removing the solvent by evaporation — into the hydrochloride.

EXAMPLE 6

5-(2-Acetoxyethoxy)-2-(5-nitro-1-methyl-2-imidazolyl)pyrimidine 0.29 g. (1 millimole) of 5-(2-hydroxyethoxy)-2-(5-nitro-1-methyl-2-imidazolyl)-pyrimidine hydrochloride is heated in 3 ml. of acetic anhydride to 100° C. for 1 hour. After cooling, the reaction mixture is introduced into water and the product is filtered off; m.p. 148°–150° C.

EXAMPLE 7

5-Ethyl-4,6-dimethyl-2-(5-nitro-1-methyl-2-imidazolyl)pyrimidine 0.34 g. (2 millimoles, of 5-nitro-1-methyl-2-imidazolylcarboxamidine, 0.26 g. (2.1 millimoles) of 3-acetyl-2-pentanone, and 0.33 g. (4 millimoles) of anhydrous sodium acetate are refluxed in 4 ml. of glacial acetic acid for 4 hours. After concentrating the reaction mixture, the residue is digested with water and purified by means of preparation layer chromatography; m.p. 110° C. (from ethyl acetate).

EXAMPLE 8

4,6-Dimethyl-5-(2-acetylethyl)-2-(5-nitro-1-methyl-2-imidazoly)-pyrimidine

The compound is obtained analogously to Example 7 with 3-acetyl-2,6-heptanedione; m.p. 142° C. (from ethyl acetate).

EXAMPLE 9

2-(5-Nitro-1-methyl-2-imidazolyl)-4-methyl-5,6-dihydrobenzo[h]quinazoline

The compound is produced analogously to Example 7 with 2-acetyl-1-tetralone; m.p. 147° C. (from isopropanol).

EXAMPLE 10

4-Trifluoromethyl-2-(5-nitro-1-methyl-2-imidazolyl)-6-(2-thienyl)-pyrimidine

The compound is obtained in accordance with Example 7 with 1-thenoyl-3,3,3-trifluoroacetone. Purification is effected by recrystallization from ethyl acetate; m.p. 188° C.

EXAMPLE 11

4-Methyl-6-phenyl-2-(5-nitro-1-methyl-2-imidazolyl)-pyrimidine

The compound is obtained in analogy to Example 7 with 2-acetylacetophenone. The product is purified by recrystallization from ethyl acetate; m.p. 150° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

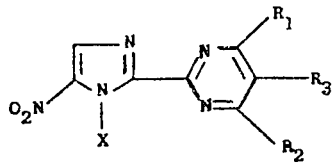

and physiologically acceptable acid addition salts thereof wherein X is alkyl of 1–4 carbon atoms, $R_1$ and $R_2$ each are a hydrogen atom, alkyl of 1–4 carbon atoms, phenyl, trifluoromethyl, or 2-thienyl, and $R_3$ is a hydrogen atom, alkyl of 1–4 carbon atoms, hydroxyalkoxy of 2–4 carbon atoms or an ester thereof of an alkanecarboxylic acid of 1–4 carbon atoms or oxoalkyl of 3–6 carbon atoms.

2. A compound of claim 1 wherein X is methyl.
3. The compound of claim 1, which is 4,6-dimethyl-2-(5-nitro-1-methyl-2-imidazolyl)-pyrimidine.
4. The compound of claim 1, which is 2-(5-nitro-1-methyl-2-imidazolyl)-pyrimidine.
5. The compound of claim 1, which is 5-(2-acetoxyethoxy)-2-(5-nitro-1-methyl-2-imidazolyl)-pyrimidine.
6. The compound of claim 1, which is 5-(2-hydroxyethoxy)-2-(5-nitro-1-methyl-2-imidazolyl)-pyrimidine hydrochloride.
7. The compound of claim 1, which is 5-ethyl-4,6-dimethyl-2-(5-nitro-1-methyl-2-imidazolyl)-pyrimidine.
8. The compound of claim 1, which is 4,6-dimethoxy-5-(2-acetyl-ethyl)-2-(5-nitro-1-methyl-2-imidazolyl)-pyrimidine.
9. The compound of claim 1, which is 4-trifluoromethyl-2-(5-nitro-1-methyl-2-imidazolyl)-6-(2-thienyl)-pyrimidine.
10. The compound of claim 1, which is 4-methyl-6-phenyl-2-(5-nitro-1-methyl-2-imidazolyl)-pyrimidine.

* * * * *